US006420176B1

(12) United States Patent
Lisziewicz et al.

(10) Patent No.: US 6,420,176 B1
(45) Date of Patent: Jul. 16, 2002

(54) COMPOSITION FOR DELIVERING DNA INTO ANTIGEN PRESENTING CELLS

(75) Inventors: Julianna Lisziewicz; Franco Lori, both of Bethesda, MD (US)

(73) Assignee: Genetic Immunity, LLC., Washington, DC (US)

( * ) Notice: Subject to any disclaimer, the term of this patent is extended or adjusted under 35 U.S.C. 154(b) by 0 days.

(21) Appl. No.: 09/153,198

(22) Filed: Sep. 15, 1998

Related U.S. Application Data

(60) Provisional application No. 60/058,933, filed on Sep. 15, 1997.

(51) Int. Cl.[7] ........................ C12N 15/09; C12N 15/63; A61K 48/00; A61K 35/00
(52) U.S. Cl. ...................................................... 435/455
(58) Field of Search ..................... 536/23.1; 424/93.1, 424/208.1, 184.1; 514/44; 435/320.1, 325, 235.1, 455

(56) References Cited

U.S. PATENT DOCUMENTS 6,013,240 A    1/2000   Behr

OTHER PUBLICATIONS

Cara et al., Self–limiting, cell–type–dependent replication of an integrase–defective human immunodeficieny virus type 1 in human primary macrophages but not T lymphocytes, 1995, Virology, vol. 208, pp. 242–248.*
Diebold et al., Gene–modified dendritic cells by receptor–mediated transfection, 1998, Gene Therapy of Cancer, pp. 449–455.*
Boussif et al., A versatile vector for gene and oligonucleotide transfer into cells in culture and in viv: Polyethylenimine. 1995, Proc. Natl. Acad. Sci. USA, vol. 92, pp. 7297–7301.*
Stahl et al., The Mannose Receptor is a pattern recognition receptor involved in host defense, 1998, Current Opinion in Immunology, vol. 10, pp. 50–55.*
Adachi et al., Production of acquired immunodeficiency syndrome–associated retrovirus in human and nonhuman cells transfected with an infectious molecular clone, 1986, Journal of Virology, pp. 284–291.*
Ridge, et al., Neonatal Tolerance Revisited: Turning on Newborn T Cells with Dendritic Cells, Science 271: 1723–1726 (1996).
Sarzotti, et al., Induction of Protective CTL Responses in Newborn Mice by a Murine Retrovirus, Science 271: 1726–1728 (1996).
Clerici, et al., T–cell proliferation to subinfectious SIV correlates with lack of infection after challenge of macaques AIDS 8: 1391–95 (1994).
Rowland–Jones, et al., HIV–specific cytotoxic T–cells in HIV–exposed but uninfected Gambian Women Nature Med 1: 59–64 (1995).
Arthur, et al., A comparison of gene transfer methods in human dendritic cells, Cancer Gene Therapy 4:17–25 (1997).
Song, et al., Antigen Presentation in retroviral vector–mediated gene transfer in vivo, Proc Nat Acad Sci USA 94: 1943–8 (1997).
Watts, C., Inside the gearbox of the Dendritic Cell, Nature 338: 724–725 (1997).
Pollard, et al., Polyethylenimine but Not Cationic Lipids Promotes Transgene Delivery to the Nucleus in Mammalian Cells, J. Biol Chem 273:13 7507–7511 (1998).
Takahashi, et al., Cell Tissue Res 292:2 311–23 (1998).
Stahl, et al., Receptor–Mediated Pinocytosis of Mannose Glycoconjugates by Macrophages: Characterization and Evidence for Receptor Recycling, Cell 19: 207–215 (1980).
Goldstein, et al., Receptor–Mediated Endocytosis: Concepts Emerging from the LDL Receptor System, Annu Rev Cell Biol 1:1 (1985).
Engering, et al., The mannose receptor functions as a high capacity and broad specificity antigen receptor in human dendritic cells Eur J Immunol 27: 2417–2525 (1997).
Canque, et al., The Effect of In Vitro Human Immunodeficiency Virus Infection on Dendritic–Cell Differentiation and Function, Blood 88:11 4215–4228 (1996).
Bender, et al., Improved Methods for the generation of dendritic cells from nonproliferating progenitors in human blood, J Immunol Methods 196:2 121–35 (1996).
Zanta, et al., In Vitro Gene Delivery to Hepatocytes with Galactosylated Polyethylenimine, Bioconjugate Chem 8:6 839–844 (1997).
Condon, et al., DNA–based immunization by in vivo transduction of dendritic cells, Nature Medicine 2:10 1122–1128 (1996).
Reiser, et al., Transduction of nondividing cells using pseudotyped defective high–titer HIV type 1 particles, Proc Natl Acad Sci USA 93: 15266–15271 (1996).

* cited by examiner

Primary Examiner—Michael C. Wilson
(74) Attorney, Agent, or Firm—Valerie E. Looper

(57) ABSTRACT

A molecular delivery complex specific to antigen-presenting cells is formed from a a non-viral gene delivery system complexed with foreign genetic material. The complex then enters the targeted cells through a specific receptor and overcomes the degradation mechanism, so that functional uptake of the foreign genetic material, or transduction, of the cell, results in gene expression. The invention also includes a method for genetic immunization without a needle.

14 Claims, 7 Drawing Sheets

(1 of 7 Drawing Sheet(s) Filed in Color)

COMPOSITION FOR DELIVERING DNA INTO ANTIGEN PRESENTING CELLS

This application is a continuation-in-part of U.S. Ser. No. 60/058,933, filed Sep. 15, 1997, which is incorporated herein as if set forth in full.

FIELD OF THE INVENTION

The present invention relates generally to methods and compositions for delivering foreign genetic material into cells. Specifically, it relates to a technique for receptor-mediated delivery of genes to cells. A gene delivery complex compatible with a specific type of targeted cell is formed from the foreign genetic material, a vector, and optionally, a carrier. The complex is then exposed to the cells under conditions permitting receptor-mediated endocytosis, resulting in the functional uptake, or transduction, of the foreign genetic material. The method is not only useful for in vitro, but also in vivo gene delivery to antigen presenting cells, specifically described as transcutaneous gene transfer to skin Langerhans cells. This technique is particularly useful for preventive and therapeutic genetic immunization when the foreign genetic material is an immunogen such as DNA encoding a substantial portion of the antigens and particles associated with an infectious virus, and where delivery by injection is undesirable.

BACKGROUND OF THE INVENTION

The immune system for animals has two different but related responses, the cellular immune response and the humoral immune response. The cellular immune response produces T lymphocytes which kill cells having foreign identifying markers on their surface. Cells which have such identifying markers on their surface are said to "present" an antigen, and are referred to as antigen presenting cells (APCs). In addition, T lymphocytes also stimulate the humoral response by helping B cells, the precursors of plasma cells.

The humoral immune response results in the production by plasma cells of antibodies which act on specific molecules in solution. Antibodies (or immunoglobulins) are proteins synthesized by an animal in response to the presence of a foreign substance. They are secreted by plasma cells, which are derived from B lymphocytes (B cells). These soluble proteins are the recognition elements of the humoral immune response. Each antibody has specific affinity for the foreign substance that stimulated its synthesis. That is, the antibody has a segment or site, called an antigen binding site, which will adhere to the foreign substance. A foreign macromolecule capable of eliciting the formation of antibodies against itself is called an antigen. Proteins and polysaccharides are usually effective antigens. The specific affinity of an antibody is not for the entire macromolecular antigen, but for a particular site on it called the antigenic determinant or epitope. Antibodies recognize foreign molecules in solution and on membranes irrespective of the molecule's context. The humoral immune response is most effective in combating bacteria and viruses in extracellular media. (The word humor is the Latin word for fluid or liquid.) One strategy for conferring immunity against disease is to expose the individual to one or more antigens associated with a virus or bacterium rather than use the actual virus or bacterium. Such a vaccine is known as a subunit vaccine, and it works particularly well to stimulate the production of antibodies.

T cells mediate the cellular immune response. In contrast to the humoral immune response, the cellular immune response destroys virus-infected cells, parasites, and cancer cells. The surface of T cells contain transmembrane proteins called T cell receptors that recognize foreign molecules on the surface of other cells. That is, T cells recognize antigen presenting cells (APCs). T cell receptors do not recognize isolated foreign molecules. The foreign unit must be located on the surface of a cell, and must be presented to the T cell by a particular membrane protein, one encoded by a highly variable chromosomal region of the host known as the major histocompatibility complex (MHC). The MHC encodes three classes of transmembrane proteins. MHC Class I proteins, which are expressed in nearly all types of cells, present foreign epitopes to cytotoxic T cells. MHC Class II proteins, which are expressed in immune system cells and phagocytes, present foreign epitopes to helper T cells. MHC Class III proteins are components of the process know as the complement cascade.

There are a variety of T cells, including cytoxic T lymphocytes (CTL, or killer T cells) which destroy cells which display a foreign epitope bound to an MHC protein. When the foreign-epitope-plus-MHC-protein binds to the T cell receptor, the T cell secretes granules containing perforin, which polymerizes to form transmembrane pores, thereby breaking the cell open, or inducing cell lysis. Other classes of T cells, called Helper T cells, secrete peptides and proteins called lymphokines. These hormone-like molecules direct the movements and activities of other cells. Some examples are Interleukin-2 (IL-2), Interleukin-4 (IL-4), Interferons, Granulocyte-Macrophage colony-stimulating factor (GM-CSF), and Tumor necrosis Factor (TNF). The T cells are implicated in the complement cascade, a precisely regulated, complex series of events which results in the destruction of microorganisms and infected cells. More than fifteen soluble proteins co-operate to form multi-unit antigen-antibody complexes that precede the formation of large holes in the cells' plasma membrane.

Expression of foreign genes in antigen presenting cells (APC) may be used to generate efficient CTL response in animals. Therefore, gene transfer and genetic modification of APC has potential to generate effective vaccine and therapeutic approaches against different diseases, including viral infections and cancer. Live recombinant virus vectors expressing various foreign antigens, such as pox viruses, adenoviruses, and retroviruses, can be used to elicit both humoral and cellular immune response by mimicking viral infection. Also, live attenuated (or, weakened) viruses have been proposed as vaccines. DNA vaccination strategy is also being explored. Different viral genes have been cloned into plasmid DNA and injected into muscles, skin, or subcutaneously. These constructs are able to express proteins and elicit both a cellular and humoral immune response.

It has been suggested that viral diseases may be responsive to the technique of genetic immunization. Certain cells, such as dendritic cells, are known to pick up antigens and migrate from the tissues of the body to the lymphoid tissues. There these cells present the antigens in the lymphoid organs: that is, they display a foreign epitope bound to an MHC protein. Such antigen-presenting cells (APCs) are a known part of the immune response mechanism. If cells such as a dendritic cells (DC) are modified so that they contain DNA encoding a virus which is infectious but incapable of efficient reproduction, they could not only present antigens in the classic sense, but also be manipulated to produce, or express, viral particles and a wide variety of viral proteins. A novel technology has been described in U.S. Ser. No. 08/803,484 "Methods and Compositions for Protective and Therapeutic Genetic Immunization" which is incorporated herein by reference as if set forth in full. It discloses that genes of a replication-incompetent virus can be incorporated into antigen presenting cells which then migrate to the lymphoid organs and produce the full complement of viral antigens and viral particles, thereby triggering both humoral and cellular immune responses. It teaches that DC in the lymphoid organs may then express all viral antigens and produce "authentic looking" viral particles. These viral particles would therefore play a pivotal role in the generation of additional immune responses.

This reference describes in Example 13 "in vivo transduction" of cells including APC. In that example, several well known methods including viral and non-viral gene delivery are exemplified. In Example 14 "in vivo transduction" of cells including APC are described. These utilize (1) direct DNA injection; (2) injection of liposomes or virosomes containing the DNA; (3) direct intersplenic injection of Class 4 pox viruses; and (4) rectal and vaginal suppositories carrying gene delivery vehicles. However, this reference did not describe in detail the methods of in vitro and in vivo gene delivery. That is the subject of the present invention.

There is some evidence suggesting that genetic modification of APC will be effective to vaccinate both neonatal and adult animals and humans. Ridge et al. (Science 271: 1723–1726, 1996) have injected DC expressing a foreign antigen isolated from another animal intravenously into mice. Both neonatal and adult mice injected with these DC were able to generate good CTL killing of target cells. These experiments also demonstrated that DC expressing a foreign antigen can induce protective cell-mediated immune response which is able to eliminate infected cells in case of viral infections. In addition, these experiments demonstrated that DC-mediated immunization of neonates may be possible. These experiments did not use genetically modified cells, nor did they utilize several foreign antigens nor a virus as described in the present invention.

Sarzotti et al. (Science 271: 1726–128, 1996) demonstrated that low dose inoculation with viruses results in a protective immune response (Th1-type) which generates CTL response but high dose inoculation will result in a nonprotective (Th2-type) immune response which mainly generates antibodies. These CTL responses were very long lasting and also could be generated in neonates. High doses of virus might overwhelm and disarm T-cells before DC could activate the T-cells. Again, the route of administration, not through injection but through presentation by DC, is important. These findings are consistent with other results showing that exposure to low dose viruses provokes predominantly cellular (Th1-type) immune response. In macaques, a low dose SIV primed the Th1-type response without antibody production and protected animals against high dose challenge (Clerici et al. AIDS 8: 1391–1395, 1994). In humans, similar results were demonstrated by Rowland-Jones et al. (Nature Med 1: 59–64, 1995)

The process of modification of cells so that they contain foreign genetic material is called gene transfer, transfection or transduction. None of the papers cited herein have presented evidence of efficient gene transfer to antigen presenting cells, either in vitro or in vivo. As background for gene transfer into antigen presenting cells such as DC, several "low efficient" in vitro methods have been described, including liposome-mediated gene transfer; electroporation and retrovirus-vector- and adenovirus-vector-mediated gene transfers (Arthur, J. F et al. Cancer Gene Therapy. 4:1 17–21, 1997, Song, E. S. et al. Proc Natl Acad Sci U S A 94:5, 1943–8, 1997). All of these in vitro methods involve the isolation of large populations of cells which are treated in the laboratory with a gene delivery vehicle. All human or animal applications involve the reintroduction of these genetically modified cells. Therefore, in vitro gene delivery methods are not feasible for vaccination or treatment of large numbers of individuals. Known in vivo methods include intradermal or intramuscular injection of recombinant virus vectors and intradermal, subcutaneous and intramuscular injection of plasmid DNA. None of these methods have been shown to effectively deliver genes into antigen presenting cells, such as dendritic cells, much less delivery of genes through the skin into the Langerhans cells.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE DRAWINGS

Figure 1:
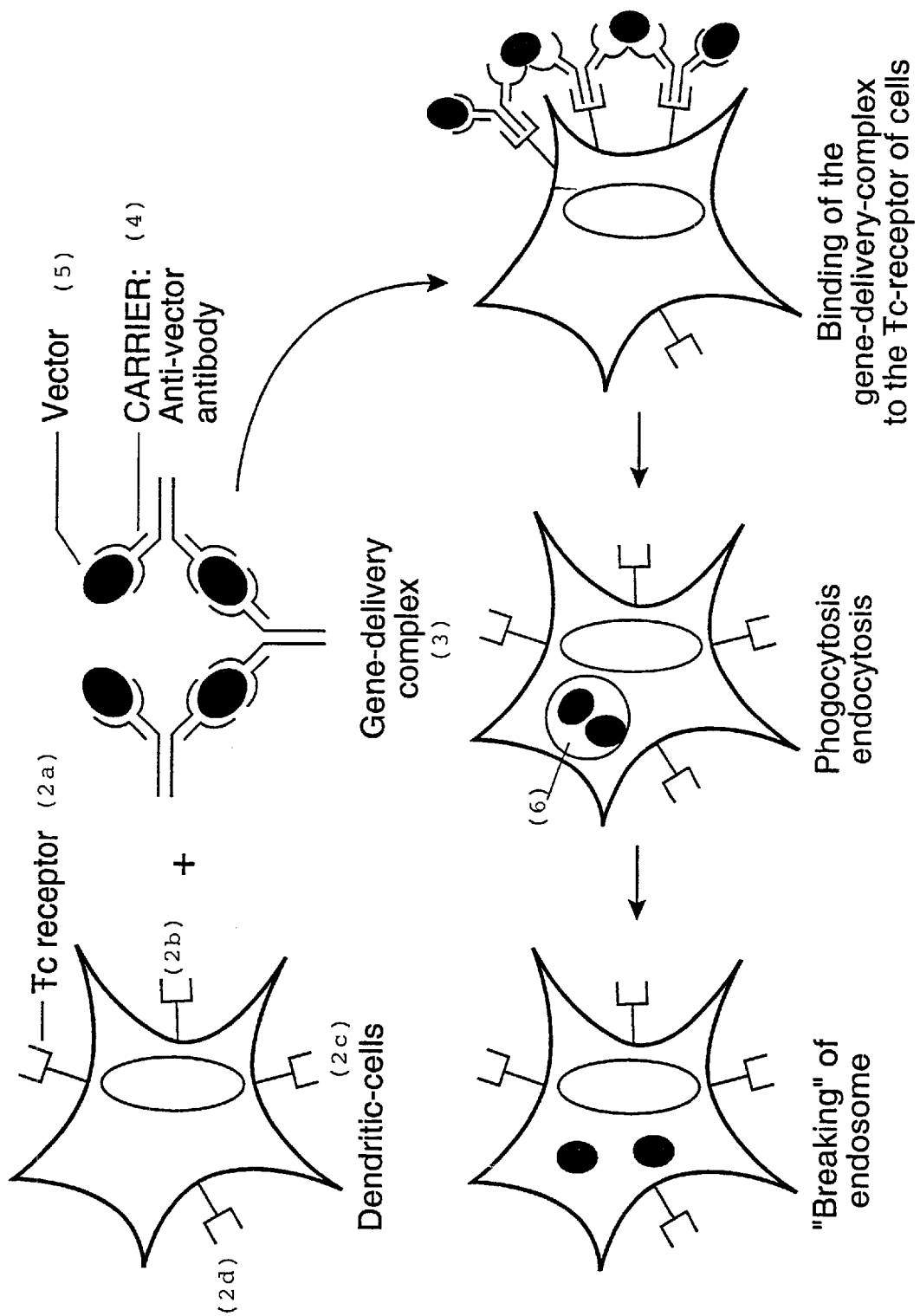
FIG. 1 illustrates antibody mediated gene delivery into cells expressing Fc-receptors.

In FIG. 1, the process for antibody mediated gene delivery into cells expressing Fc-receptors is illustrated conceptually. Target cells (1) having one or more receptors (2a,b,c,d) are exposed to a gene-delivery complex (3) comprising a carrier (4) and a vector (5) which includes the foreign genetic material. The gene delivery complex (3) binds to the receptors (2a,b,c,d) of the cell (1) and the vector (4) is incorporated into the cell via endocytosis or phagocytosis in an endosome (6). The vector (4) has the property of breaking the endosome (6), allowing the foreign genetic material to be released into the cell.

Figure 2:
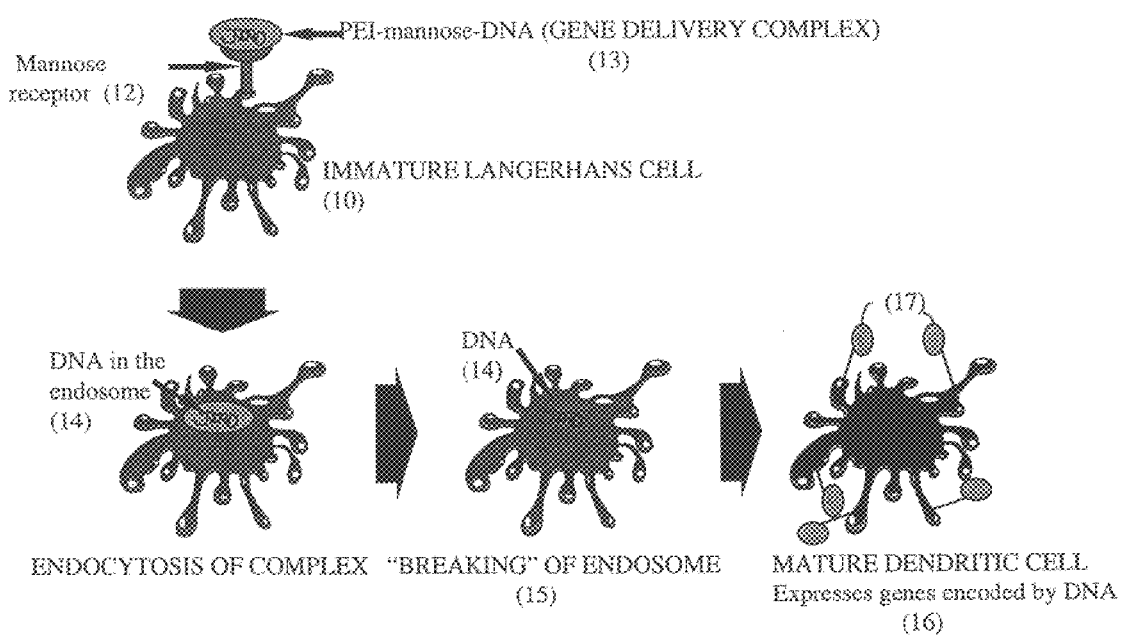
FIG. 2 illustrates gene delivery into dendritic cells and Langerhans cells via the mannose-receptor using PEI-man-DNA complex

In FIG. 2, the process for sugar-mediated gene delivery into cells expressing mannose-receptors is illustrated conceptually. Target cells (10), in this case, immature Langerhans cells having one or more mannose-receptors (12) are exposed to a gene-delivery complex (13) comprising a polyethylenimine-sugar (mannose) complexed with the foreign genetic material. The gene delivery complex (13) binds to the receptors (12) of the cell (10) and the PEI-man-DNA is incorporated into the cell via endocytosis in an endosome (14). The vector (PEI-man) has the property of breaking (15) the endosome, allowing the foreign genetic material to be released into the cell. The cell matures (16) and expresses proteins (17) coded by the foreign genetic material.

Figure 3:
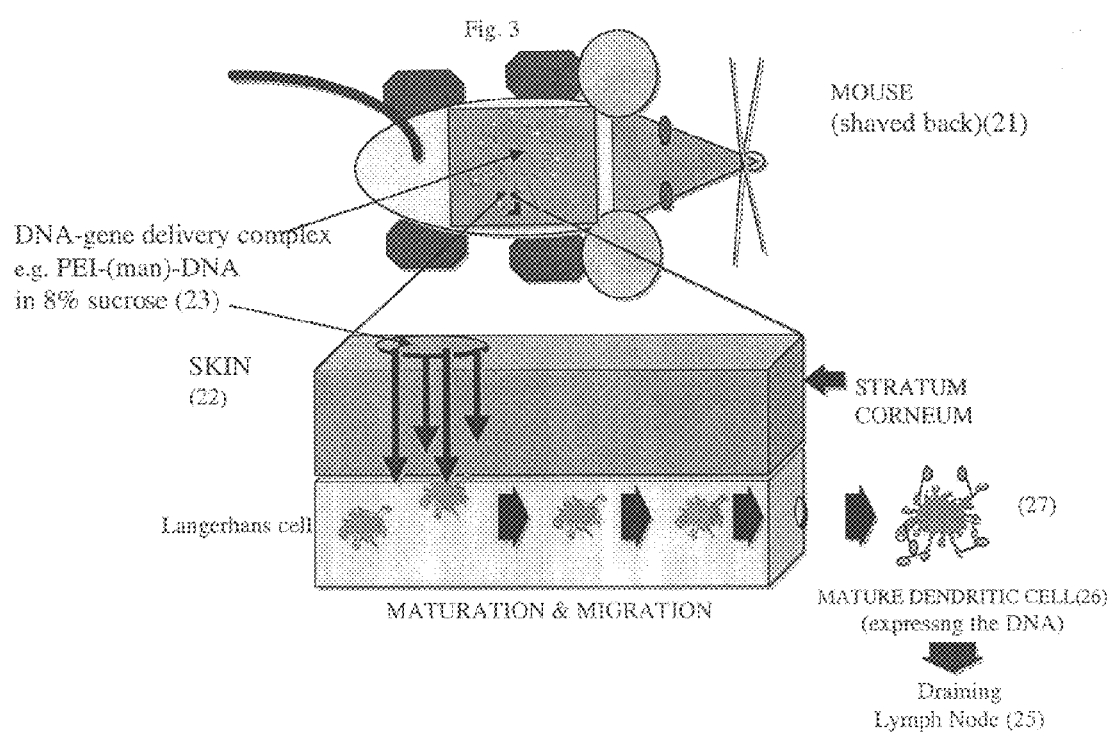
FIG. 3 illustrates the transcutaneous gene delivery approach FIG. 4 compares effectiveness of in vitro transfection of human DC using two different complexes of the present invention.

In FIG. 3, the experiment demonstrating in vivo the sugar-mediated gene delivery into cells expressing mannose-receptors is illustrated. Target cells are Langerhans cells in the skin known to express mannose receptors. Mice (21) were anesthetized and an area on the back of each mouse (22) was shaved. The shaved surface with ethanol. PEI-man-DNA gene delivery complex in 8% glucose (23) was applied to the shaved area (22) of each mouse. Langerhans cells (24) found in the shaved area of the skin (22) pick up the complex as described in FIG. 2 above, get activated and migrate (24) to the draining lymph node (25). During the migration Langerhans cells (24) mature to be dendritic cells (26) and express the protein (27) encoded by the DNA.

Figure 4:
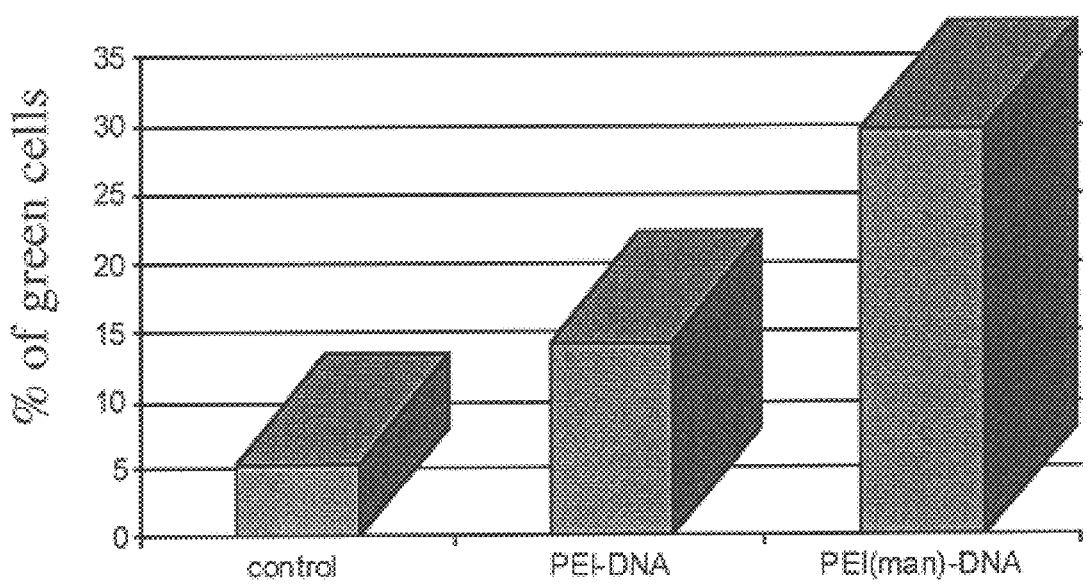

In FIG. 4, experimental results are demonstrating the in vitro gene delivery with PEI-DNA vs. PEI-man-DNA complexes. Human DC were cultured as described in the text and transfected with complexes. A marker gene encoding a green fluorescent protein (GFP) was used as the DNA. In these experiments the complexes were dissolved in a solution of NaCl. The experiment demonstrated that PEI-man is more efficient to transfect cultured DC than PEI.

Figure 5:
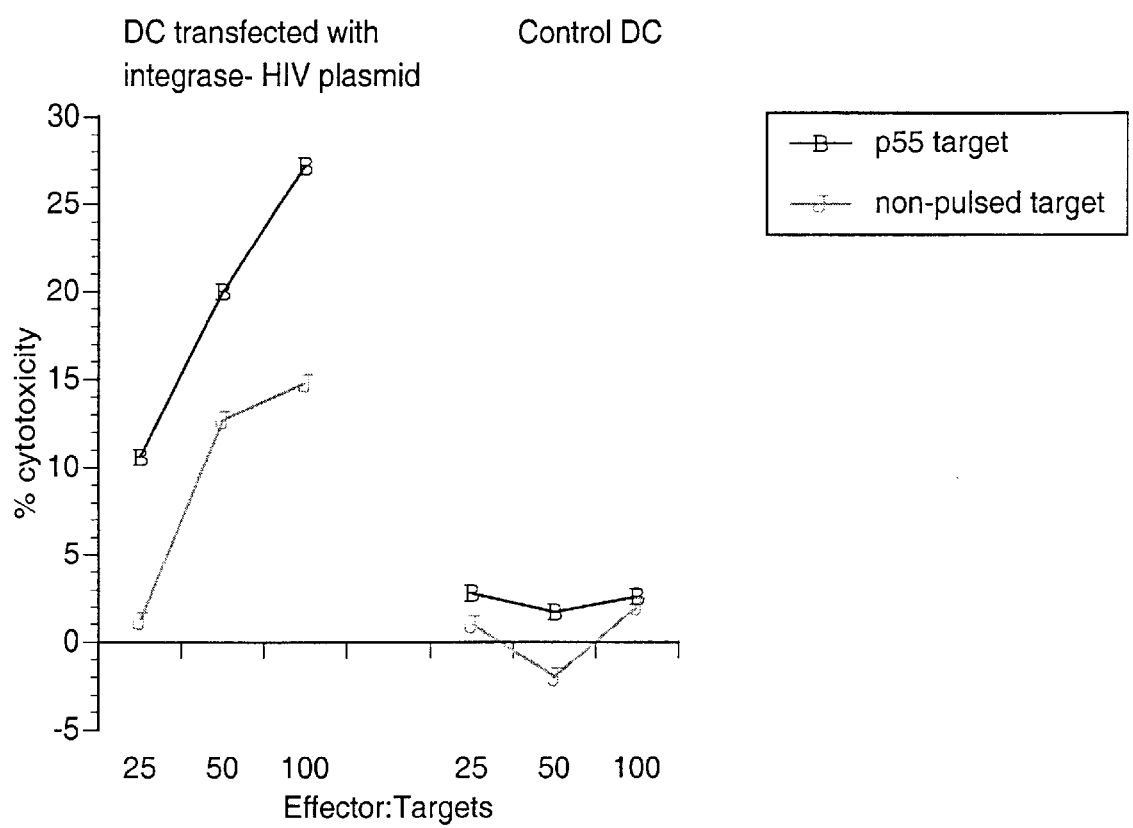
FIG. 5 CTL assay, illustrates that transduced DC are able to generate cytotoxic T cells from naive T cells: compares % cytotoxicity of DC transfected with integrase-HIV plasmid to that of control DC.
Figure 6:
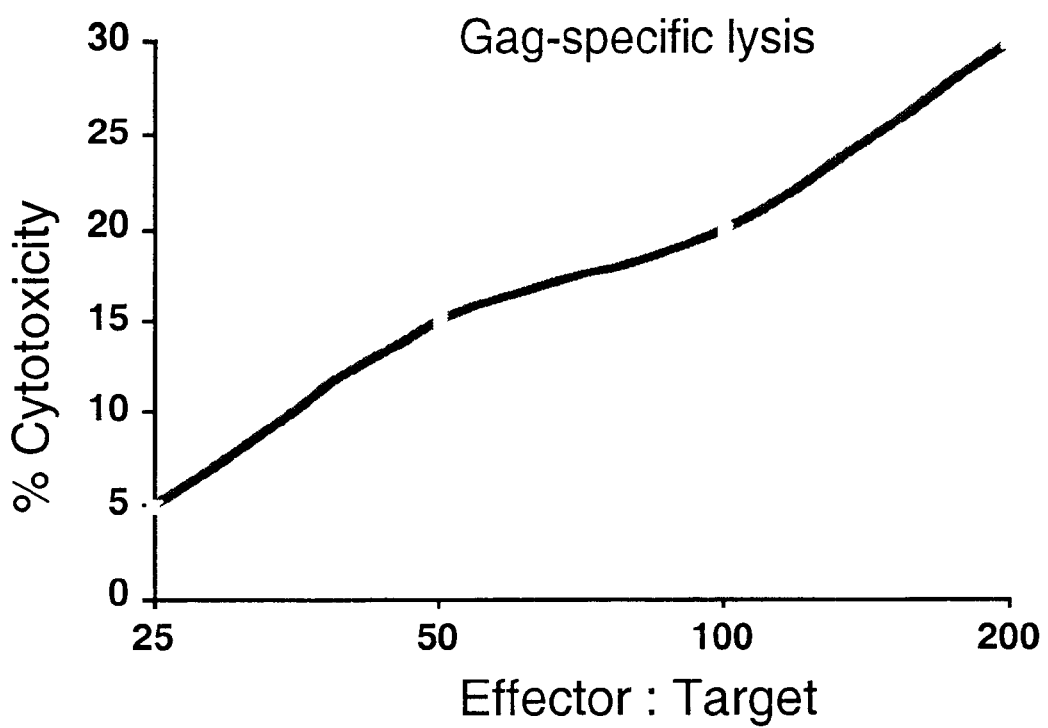
FIG. 6 illustrates the CTL response after ex vivo genetic immunization compares CTL response obtained in vivo using transfected DC.

FIGS. 5–6 report experimental results and are discussed in detail in the Example section, below.

FIGS. 7A–7D reports experimental evidence that transcutaneous transduction of Langerhans cells results in migration of the cells and expression of the transferred gene. The figure is a series of color photographs which records green cells having DC morphology and expressing the green fluorescent protein, which is the product of the gene which was transferred via skin delivery. Panel A is a sample of a lymph node from a control mouse at 200× magnification. It exhibits a normal amount of background fluorescence. The same is true of Panel C, except that the magnification is 400×. Panel B is a sample from a lymph node of a mouse that was immunized by the transcutaneous application of a PEI-mannose-DNA complex. Panel D is the same as Panel B, except that the magnification is 400×. The fluorescence exhibits the bumpy morphology characteristic of dendritic cells expressing proteins.

SUMMARY OF THE INVENTION

It is an object of the present invention to provide a method of improved efficiency of gene transfer to cells, in vitro and in vivo. A further object of this invention is to provide an improved method of genetic immunization by increasing the efficiency of gene transfer to antigen presenting cells. It is yet a further object of this invention to provide a means of stimulating both humoral and cellular immune responses to the protein product of the transferred genetic material. Yet another object of this invention is to provide an effective immune response to viral diseases. Yet another object of this invention is to provide a vaccine for viral diseases which is effective and has improved safety. An advantage of the present invention is that it provides a in vivo gene transfer method which can be utilized for immunotherapy and vaccination for a wide variety of diseases.

An another advantage of the present invention is that it can utilize any type of DNA, or RNA, including plasmid DNA encoding immunogens like oncogens, immunogens (causing allergy), viral proteins or different types of replication defective viruses, defective viral particles, as well as plasmid DNA.

An another advantage of the present invention is that it can utilize instead of DNA proteins like oncogenic protein (e.g. mutated p53 or Ras), immunogens (causing allergy), viral proteins or different types of replication defective viruses.

These and other objects and advantages of the present invention will become apparent through the text and examples herein.

The objects and advantages of the present invention are achieved by forming a gene delivery complex comprising a vector (which contains the desired foreign genetic material) and a carrier (which can bind both to the cells and to the gene delivery particle), then exposing target cells to the complex under conditions permitting endocytosis. The vector has the characteristic that it allows the genetic material to escape from endosomal degradation and it delivers the desired foreign genetic material to either the cytoplasm or to the nucleus. Foreign proteins can be expressed and presented to the immune system by the genetically modified cells. If the foreign genetic material encodes a replication defective virus as described in U.S. Ser. No. 08/803,484 "Methods and Compositions for Protective and Therapeutic Genetic Immunization" which is incorporated herein as if set forth in full, the altered target cells may then present viral antigens and also express viral particles and proteins in the lymphoid organs, thereby generating an effective cellular immune response as well as a humoral immune response.

DETAILED DESCRIPTION OF THE INVENTION

The subject invention most closely concerns methods and compositions for the delivery of foreign genetic material into cells. It is particularly useful to enhance the efficiency of genetic immunization by increasing the efficiency of gene transfer to certain cells participating in the immune system, such as antigen presenting cells (APCs). Although the goal of the inventors is to deliver genetic material into cells, the inventors contemplate that any molecule of suitable size and configuration can be delivered into cells using the present invention. Thus, other materials such as drugs or proteins, for example, can be delivered to targeted cells using the techniques described herein.

The present invention takes advantage of some of the natural pathways available in animals.

It is known, for example, that specific proteins are imported into cells by a process called receptor-mediated endocytosis. In this process, specific proteins, or ligands, bind to specific receptors in the plasma membrane of a cell. The membrane forms a vesicle, or pocket, around the protein and eventually internalizes the ligand. That is, it imports the protein into the cell. Afterward the endosome typically delivers these complexes to a lysosome where they are digested into their component parts, peptides. In cells where MHC expression occurs, peptide-MHC complexes accumulate in the lysosome and then reach the surface of the cell in a process called antigen presentation. Receptor-mediated endocytosis is the means of delivering large molecules such as essential metabolites, hormones and growth factors to cells. It is a pathway exploited by many viruses and toxins to gain entry into cells, and also plays a part in the immune response. For example, phagocytic cells have receptors enabling them to take up antigen-antibody complexes.

Particles complexed with antibodies such as IgG or complements such as C3b, or both, can efficiently enter into cells through receptor-mediated endocytosis and phagocytosis. Antibodies, or immunoglobulins, have different portions that allow them to perform different functions. For example, Immunoglobulin G (IgG) is a Y-shaped molecule with two $F_{ab}$ segments having antigen binding sites and an $F_c$ segment which mediates effector functions. Multivalent antigens can bind to antibodies and form immune complexes. The size of these immune complexes is a function of the relative concentration of antigen and antibody.

Endocytosis can be enhanced by a process known as opsonization. Opsonization is a process whereby antibodies coat antigens, thereby providing a means for other components of the immune system to recognize and respond to the antigens. Immunoglobulins with the appropriate $F_{ab}$ sites can be used to coat the antigen particles, and subsequently, cells expressing the corresponding $F_c$ receptors can recognize the $F_c$ part of the opsonized antigens and readily endocytose them. Complements such as C3b, C4b and C3bi also have opsonization activity. Larger immune complexes are more effectively phagocytosed than small ones by cells such as B-cells, mononuclear phagocytes, granulocytes, neutrophils and dendritic cells expressing receptors for the $F_c$ portions of immunoglobulin molecules.

IgG antibodies can be made in animals by injecting the antigen with or without adjuvants. Also, antibodies can be cloned and humanized using molecular genetic techniques. Other receptors that are commonly located on the membranes of immune system cells include, for example, transferrin, mannose and asialoglycoprotein receptors, which could easily be used for the transduction of immune system cells. The $F_c$ receptor part of the antibody can also be replaced with other receptor-binding domains using molecular genetic techniques. For the inventors' present purpose, the $F_c$ receptors and corresponding IgG molecules are convenient, as these serve the further function of transporting genes to dendritic cells.

Once a molecule or particle is taken up into a cell via endocytosis or phagocytosis, it is contained in a protein-receptor complex called an endosome. Endosomes are intracellular acidic compartments that serve a sorting function. Phagosomes, which result from phagocytosis, are large (10x–20x) endosomes. Endosomes then fuse with lysosomes where the material is digested to smaller products such as peptides, nucleotides and sugars. In the present invention, the role of the vector is to provide the foreign gene to the cell and avoid degradation of the gene. That is, the vector must be able to break the endosome and release the gene into the intracellular fluid, cytosol, or onto the nucleus. A number of particles are known to be able to break the endosome after receptor-mediated endocytosis, including viral gene delivery particles such as adenovirus vectors, retrovirus vectors, pox-virus vectors, and SV-40 virus. Non-viral gene delivery particles include conjugates of DNA with polylysine, polyethylenimine and its derivatives, liposomes, virosomes and chemicals which increase the pH in the endosome, such as chloroquine.

Target Cells

This invention can be used with any cells capable of receptor-mediated endocytosis or phagocytosis. The target cells must express a receptor site which, upon binding with a complementary molecule, can bring the desired molecule into the endosome or phagosome. For the inventor's present purpose, such cells are preferably cells which participate in the immune response. They include cells which can engage in receptor-mediated endocytosis and phagocytosis of antigens. Such cells include, for example, B-cells, mononuclear phagocytes, granulocytes and dendritic cells. These cells express receptors for the Fc portion of immunoglobulins or complement receptors, or both. Dendritic cells and macrophages are particularly preferred, because they can efficiently present foreign antigens, thereby provoking cellular immune response, or CTL response. The cells can also be targeted through other receptors such as the transferrin and mannose receptors.

Dendritic cells reside in the lymphoid tissues, such as the spleen, tonsils and lymph nodes, but they can be found in the blood, epidermis, mucosa, and other peripheral tissues. These cells pick up antigens and migrate with the antigens to the lymphoid tissues. In the skin, dendritic cells called Langerhans cells can be found in the epidermis. When they endocytose an antigen, they migrate into regional lymph nodes. In the lymph node they are called interdigitating cells, and they present the antigen to naive T-cells, provoking the cellular immune response.

To increase the efficiency of gene transfer, the number of available dendritic cells should be maximized. Choice of location can be a factor. High concentrations of dendritic cells are found, for example, in the skin and on mucosa, such as the mouth, vagina and rectum. Immature DC in the tissues can efficiently endocytose, therefore they are a good target of the gene delivery complex which delivers genes with receptor-mediated endocytosis. However, for efficient expression of MHC molecules and antigen presentation, DC must also be activated. In vitro, immature DC can be generated from peripheral blood with GM-CSF and IL-4 or from bone marrow precursors with GM-CFS. Activation of these immature DC can be induced in vitro and in vivo by bacterial products such as lipolysaccharid and TNF-alpha (Watts C. Nature 338: 724–725, 1997).

Dendritic cells can be attracted to a specific location and activated by an event implicating the immune system such as a cell or tissue injury. For the present purpose, attraction and activation of antigen presenting cells, including dendritic cells, can be mediated by an immune response unrelated to vaccination or viral infection. An example would be the skin rash that is the result of contact sensitivity to chemicals such as drugs and toxins, cosmetics and environmental antigens. If a chemical irritant is swabbed onto the skin, a rash or lesion will usually appear 24–48 hours after exposure. The lesion is due to neoantigens created by binding chemicals to the surface proteins of Langerhans cells. Neoantigens are covalently modified "normal" proteins (e.g. phosphorilated) which are recognized by antibodies. At this site, higher than normal amounts of dendritic cells may be found, and they are more likely to be activated, that is, more receptive to immediate endocytosis of an antigen. The choice of irritant depends on its efficacy to attract DC and on its side effects. In another embodiment of the invention, an immune complex-mediated injury can be created. In that case, immune complexes with both antigen and antibody components can be used to activate B cells and the complement cascade with resultant tissue injury.

Since the cells are targeted through a specific class of receptors, a particular advantage of this invention is that the gene delivery complex can be made to target specific cells. If the gene delivery complex is made with IgG or a polyethylenimine modified with an appropriate starch or sugar, it will be taken up mainly by antigen presenting cells. This would be a great advantage in the development of gene-based vaccines. Targeting other cells expressing, for example, complement receptors or transferrin receptors is also feasible as described above.

Gene Delivery Complex

The gene delivery complex of the present invention can be used to deliver genes in vitro or in vivo to cells carrying a given receptor. The gene delivery complex is built from two parts: the genetic material and a delivery particle, and may further comprise a carrier (See FIG. 1). In one embodiment, the genetic material is derived from an attenuated HIV virus and the delivery particle is non-viral vector.

In another embodiment, the same or different genetic material may be combined with a viral vector and a carrier. In that instance, the carrier is preferably an antibody that has a site complementing a receptor present on the surface of the target cell, and an antigen binding site specific to the desired delivery particle. Such a carrier is specific to both the cell and the delivery particle. For genetic immunization, human IgG specific to the gene delivery particle is conveniently selected. If there is no antibody commercially available, it can be made with techniques known to one of ordinary skill in the art. If the gene delivery particle is replication-defective HIV-1, human IgG can be used as a carrier, and is available in large quantities for passive immunotherapy. The gene delivery particle can be complexed with the antibody by incubating them together for 5 minutes at room temperature. The relative amounts of gene delivery particle and antibody are determined by whether it is desired to opsonize the gene delivery particles.

The Genetic Material

The genetic material, either DNA or RNA, is carried by the delivery complex. One or more genes can be encoded on a strand of plasmid DNA, on double-stranded DNA or on RNA. Alternatively, the genetic material can be built into recombinant viruses if they are used as a gene delivery particle. If the purpose of the gene transfer is to induce an immune response, then the genetic material must express one or more immunogenic proteins. Transduced cells will subsequently express enough of the immunogenic proteins (different viral antigens and produce authentic enough viral particles) to provoke a sufficient immune response (e.g., protect the individual from infection by the wild-type virus).

The choice of the gene delivery particle will be determined by the disease and the choice of gene(s) to transfer. Where it is desired to construct a vaccine for a reverse-transcriptase dependent virus such as IIIV, the DNA preferably encodes at least a substantial portion of a replication-or integration defective virus or the replication- or integration-defective virus itself. Examples include but are not limited to integrase negative mutants of a dual-tropic primary isolate such as HIV-1/LW, and derivatives thereof having a deletion in the protease cleavage site of the gag gene or where the DNA further includes one or more stop codons in one or more reading frames of the integrase gene. See Methods and Compositions for Protective and Therapeutic Genetic Immunity, U.S. Ser. No. 08/803,484 filed Feb. 20, 1997 and incorporated by reference as if set forth in full. Where it is desired to construct a vaccine for cancer, the immunogen is preferably DNA encoding one or more oncogens. Other DNA constructs can be DNA encoding replication defective Human Papilloma Virus (causing cervical cancer), replication defective Hepatitis A, B and C viruses (causing hepatitis and liver cancer), and DNA encoding replication defective animal viruses like Bovine Leukemia Virus or Feline Immunodeficiency Virus. Choices for a delivery particle incorporating the foreign genetic material can include: (a) replication defective HIV or other retrovirus; (b) recombinant adenovirus; (c) plasmid or linear DNA or RNA complexed with PEI or a derivative of PEI; (d) a virosome containing any DNA or RNA; (e) liposome containing DNA or RNA; (f) plasmid DNA-polylysine virus complex; (g) sugar complexed with any DNA or RNA.

The Delivery System

In order to effectively deliver the genes to the cell, the gene delivery system must contain the gene or genes to be delivered and also must have the capacity to break the endosome (or phagosome), rather than be delivered to a lysosome or be isolated on the outside surface of a cell and targeted for destruction. Further, the gene delivery system must facilitate incorporation of the foreign genetic material into the genetic material of the cell.

The gene delivery system can include either a viral or non-viral vector. Viral gene delivery systems include recombinant virus vectors such as adenovirus vectors, retrovirus vectors, pox-virus vectors, mutant viruses (described above) and virosomes. Non-viral gene delivery systems include DNA conjugates with sugar, polylysine, polyethylenimine, polyethylenimine derivatives, and liposomes, together with their derivatives.

Non-viral gene delivery systems such as those utilizing sugars, sugar derivatives, liposomes, liposome derivatives and polyethylenimine or polyethylenimine derivatives are preferred. Of these, sugar and polyethylenimine derivatives adapted to target the mannose receptors of immune system cells are most preferred.

Non-viral gene delivery systems offer several advantages over viral gene delivery systems: 1) First, the non-viral vector is not recognized by the immune system, so no immune response is generated against it. As a result, it is more likely that individuals treated with the ultimate vaccine will tolerate and develop adequate immune response in cases of repeated immunization; 2) non-viral systems are potentially more safe that viral systems because there is no possibility that the system will mutate in an unexpected fashion; 3) non viral systems can be chemically synthesized in a large amounts, and are therefore potentially less expensive.

The preferred embodiment is based on a cationic polymer, polyethylenimine(PEI). PEI binds to DNA and makes the complex. The PEI-DNA complex can enter into the endosome of the skin's antigen presenting cells, Langerhans cells, via asialoglycoprotein receptor-mediated endocytosis. Then, the PEI component of this complex utilizes endosome buffering and swelling as an escape mechanism to the cytoplasm [Pollard H; Remy J S; Loussouarn G; Demolombe S; Behr J P; J Biol Chem Mar. 27, 1998; 273(13):7507–11]. PEI can also be modified to target other receptors. For example, a PEI derivative, such as a sugar-modified PEI, obtains similar results, except that it is taken up through the cells' mannose receptor. Such derivatives can be made in the laboratory. For example, an isothiocyanantophenyl phenyl mannose derivative can be coupled to PEI 25 kDa, yielding a ligand (or, mannose residue of low affinity for the mannose receptor, 1 mM). Another possibility is to use linear PEI 22k Da derivatized mannotenpaose ligand. (These materials were graciously supplied by Dr. Jean-Paul Behr, Laboratoire de Chimie Genetique, Faculte de Pharmacie, CNRS-UMR 7514 74 route du Rhin 67401 Illkirch, France)

The mannose receptor is a 175-kDa transmembrane glycoprotein that specifically expressed on the surface of macrophages and Langerhans cells. The ectodomain of the mannose receptor has eight carbohydrate recognition domains. The mannose receptor recognizes the patterns of sugars that adorn a wide array of bacteria, parasites, yeast, fungi, and mannosylated ligands. [Takahashi K; Donovan M J; Rogers R A; Ezekowitz R A, Cell Tissue Res 1998 May; 292(2):311–23]. In contrast to $F_c$ receptor, the mannose receptor reconstitutes itself while releasing its cargo [Stahl et al. Cell 1980 19:207]. It thus can internalize of ligands in successive rounds, in a manner similar to the transferrin receptor, providing a sustained capacity for antigen capture [Goldstein, et al, 1985, Annu Rev Cell Biol. 1:1]. It has been recently discovered that mannose-receptor-mediated uptake of antigens results in about 100 fold more efficient antigen presentation to T-cells, as compared to antigens internalized via fluid phase [Engering et al. 1997, Eur. J. Immunol. 27:2417–2425]. This enhanced antigen presentation is due to highly efficient uptake of antigens via the mannose receptor. For these reasons we believed that targeting the mannose receptor may yield both specificity for antigen presenting cells and improved efficiency of functional uptake of the complex into the endosome.

The Carrier

The carrier of the present invention is the part of the gene delivery complex which joins a gene delivery system with a cellular receptor. In one embodiment the carrier is an immunoglobulin G (IgG). IgG is a Y-shaped molecule with two $F_{ab}$ segments having antigen binding sites and an $F_c$ segment which binds to the cellular receptor called $F_c$-receptor. Immune system cells such as B-cells, mononuclear phagocytes, granulocytes and dendritic cells have $F_c$ receptors. When IgG is used as a carrier, it targets specifically cells having $F_c$ receptors.

To change the carrier specificity to target other cells, the $F_c$ part of the antibody can be replaced by other receptor binding domains, such as complement, sugar, or transferrin.

Where the carrier is an antibody large complexes are formed, the carrier and gene delivery system are preferably combined in equal proportions. Where it is desirable to opsonize the particle, the amount of the carrier greatly exceeds the amount of the gene delivery particles. Both endocytosis and phagocytosis are enhanced in the case of large complexes and opsonized particles. The gene delivery complex is preferably opsonized with the carrier. Where an opsonized gene delivery complex made of an antibody complexed with a delivery particle incorporating foreign genetic material is administered to an individual, cellular immune response will be maximized over the humoral immune response. The dendritic cells will be activated by the opsonized complexes, and endocytosis will be more efficient. Also, the multiple antibodies will block the antigenic determinants (epitopes) of the delivery particle. Therefore, no direct antibody response to the delivery particle would be expected. Also, some antibody complexed antigens will bind to the $F_c$ receptor site of B cells, further inhibiting their antibody response. However, cellular immunity would be stimulated because the complex would be endocytosed or phagocytosed by various kinds of antigen presenting cells, including dendritic cells and macrophages.

In a preferred embodiment, the carrier is covalently joined to the non viral gene delivery system. PEI can be chemically modified with sugars (e.g., mannose, glucose, galactose, etc.). The carrier in this case is the sugar ligand, which is recognized by the mannose receptor. To change the carrier's specificity, sugar can be replaced by other receptor-binding domains.

In vivo Gene Delivery

The gene delivery complex can be injected directly into the blood, skin, or other place where cells corresponding to the carrier binding specificity are located. The complex can be applied on the skin or mucosa surfaces directly. In that event, it is preferable that the Langerhans' cells are activated on the surface. Activation may be achieved by receptor stimulation (e.g., mannose receptor), toxin activation (cholera toxin), a tissue or cell injury such as inflammation, and may be the consequence of another antigenic stimulation.

The complex can be infused using a pediatric feeding tube orally, vaginally or rectally in the case of human or animal adults or neonates. Neonates may respond better to oral administration than adults. Alternatively, the gene delivery complex may be packaged in a suppository and inserted in the vagina or rectum.

Where a viral delivery particle is used, the delivery particle can be injected directly into the muscle or skin, in the presence or absence of adjuvants, of the subject on two separate occasions for high titer of antibody production in vivo. The first injection will result primarily in a humoral immune response. That is, the capability to produce large numbers of antibodies will result. Where a concentration of IgG antibodies sufficient to opsonize the delivery particles is available, (it can be measured or assessed by experience) then the delivery particle can be administered a second time as described in 1–3 above. The site of the second administration must be chosen carefully to ensure that cells are present which can phagocytose or endocytose the opsonized antigens.

Treatment of Active Infection

The vaccine of the present invention might also be used as a method of treating active HIV infection. HIV replicates abundantly, mutates rapidly, and damages the immune system. Both the rate of replication and the rate of mutation outpace the immune system's ability to respond. This means that, while the immune system is capable of mounting an effective response to a given type of HIV particle, enough new variants of the particle are produced to stay ahead of the immune system. If replication of the wild-type virus can be suppressed either before the immune system is substantially damaged or long enough to allow the immune system to recover, the vaccine of the present invention can be used to strengthen the immune system's ability to recognize the new variants of the virus, thereby providing a means of controlling viral replication in individuals that have already been infected.

Drug combinations that are effective to at least temporarily inhibit HIV replication are known. The inventors have shown that drug combinations including hydroxyurea, one or more reverse transcriptase inhibitors and, optionally, one or more protease inhibitors are particularly effective, and, for some patients, allow the possibility of stopping drug treatment for extended periods of time. See U.S. Ser. No. 09/056,691, filed Apr. 8, 1998, U.S. Pat. No. 5,977,086, "Method of Inhibiting HIV by Combined Use of Hydroxyurea, a Nucleoside Analog, and a Protease Inhibitor, U.S. Ser. No. 09/048,886, filed Mar. 26, 1998, U.S. Pat. No. 6,251,874 Method of Inhibiting HIV using Hydroxyurea and Reverse Transcriptase Inhibitor in vitro and U.S. Ser. No. 09/048,576, now abandoned filed Mar. 26, 1998, Method of Rendering a HIV Population Replication Incompetent in vivo, all of which are incorporated herein by reference as if set forth in full. The present invention includes the treatment of a patient with active HIV infection with an appropriate drug combination until the viral load in the blood has reached a suitably low level, less than about 50,000 copies per ml, preferably less than 10,000 copies per ml, more preferably less than 200–500 copies per ml. The patient is then vaccinated using the present invention while the drug combination suppresses replication of the wild-type virus.

The following Examples are presented for the purpose of illustrating the practice of the present invention. They do not limit the invention, or the claims which follow.

EXAMPLES

1. Expression of Plasmid DNA Encoding a Replication Defective HIV in Cultured DC There are several sources of DC. DC can be isolated from bone marrow CD34+ hematopoietic progenitor cells. Bone marrow mononuclear cells will be separated by Ficoll-Hypaque gradient centrifugation. These cells will be positively selected with human CD34 antibodies conjugated magnetic beads (Dynal Detachabeads) and CD34+ cells will be displaced from magnetic beads using high affinity polyclonal antibody against CD34 monoclonal antibody. These cells can differentiate to DC when they are cultured with stem cell factor, GM-CSF and TNF-alpha [Canque, B., M.

Rosenzwajg, et al. (1996). "The effect of in vitro human immunodeficiency virus infection on dendritic-cell differentiation and function." Blood 88(11): 4215–28.]

Monocyte-derived DC were generated from peripheral blood mononuclear cells in the presence of GM-CSF and IL-4. [Bender, A., M. Sapp, et al. (1996). "Improved methods for the generation of dendritic cells from nonproliferating progenitors in human blood." J Immunol Methods 196(2): 121–35.] On day 4, cells were transfected with lipofectamine complexed with plasmid DNA encoding HIV-1/LWint- (an integration and replication defective HIV described in U.S. Ser. No. 08/803,484). Lipofectamine, a commercially available cationic liposome useful as a transfection reagent (available from Gibco BRL Life Technology, PM. Gaithersburg, Md., US) 48 hours later cells were washed and analyzed. The purity of the DC, characterized by Fluorescence Activated Cell Sorter (FACS) measuring surface markers (FACS) was 90.6%. DC cell types were found to be CD3-, CD19-, CD56-, CD14- and HLA DR+ using FACS analysis. The expression of HIV-1 Gag and Env and Tat proteins was also measured by FACS in permeabilized cells. The level of non-specific binding of isotope control Ig was the same in the control transduced and specific plasmid transduced. We found in three independent experiments that 25–37% of HIV-1/LWint-tranduced DC expressed Env, Gag and Tat proteins. That is, 25–37% of the cells in the transduced samples expressed HIV proteins. Transduced and control cell samples were also double-stained with p24 and B7-2 antibodies to demonstrate that DC and not macrophages were expressing the antigen. These results were surprisingly good, because using the same methods with another plasmid DNA (CMV-driven hemagglutinin of influenza virus gene) only 5–8% of the transfected cells expressed proteins. These results demonstrated that defective HIV can be efficiently expressed by transduced DC.

2. DNA Encoding Replication Defective Viruses are More Efficient Antigens than DNA Encoding One or More Proteins In an independent experiment we compared the expression of two different HIV plasmids in DC: HIV-1/LWint- and LTR-tat. Both constructs are driven by the same promoter: HIV-1-LTR and the expression of both constructs depends on the transactivation of Tat. Transfection was performed as described in example 1 and 48 hours later expression of the Tat protein was analyzed by FACS. We found that 32% of HIV-1/LWint- plasmid transfected DC expressed Tat protein. In contrast only 10% of the LTR-tat transfected DC expressed the same Tat protein. This result was suprising, because in this comparative study we were expected the same efficiency with the two different constructs. Replication defective viruses definitly have the capability to form viral particle, which can be released from the cell. Since antigen presentation depends on gene expression in DC, this experiment clearly demonstrate that DNA encoding defective viruses are more efficient antigens than DNA encoding one or more proteins.

3. Transduced, Cultured DC Activate Naive CTL in vitro

After transduction, DC were cultured with autologous T-cells at a ratio of 1:10. After 7 days these T-cells were used as an effector to lyse (kill) a monocyte/macrophage cell population from the same donor that had been pulsed with p55, an HIV protein conveniently used as a label. This CTL activity was measured using Cr-relase assay. As FIG. 5 demonstrates, CTL induced by transduced DC lysed the target cells specifically and effectively. Because generation of CTL in vitro is more difficult than in vivo, these experiments show that cells which have been subjected to genetic immunization can activate naive CTL so that they will effectively lyse in vivo infected cells. Furthermore, the experiment further demonstrates that DNA encoding a defective virus not only express efficiently HIV genes but also can generate an effective immune response.

4. Ex Vivo Genetic Immunization with Transduced DC

To prove the in vivo efficacy of genetic immunization in monkeys, dendritic cells were generated from 40 ml peripheral blood of pigtail macaques. Cells were transfected with LW/int- plasmid using polyethylenimine as described in Example 5. The transfected DC were washed and injected into juvenile pigtail macaques 36–48 hours after transfection. One part of the transfected DC was injected subcutaneously and one part was injected intravenously. After 4 weeks and only one immunization attempt, one monkey already showed CTL response (FIG. 6), which suggests that the in vitro result can be reproduced in vivo in animals. In contrast, the HIV subunit vaccines presently approved for Phase III human clinical trials have not been shown to generate any CTL response, even after multiple immunization attempts.

5. Polyethyleneimine-mediated Gene Transfer into Cultured Dendritic Cells

Dendritic cells were transduced with plasmid encoding HIV-1/LWint- as in Example 1, except that polyethyleneimine (PEI kindly supplied by Dr. Behr) was used instead of lipofectamine. The cells were tested as in Example 1, and more than 60% of the dendritic cells transduced using polyethyleneimine expressed HIV-1 proteins in contrast to the 25–37% of cells transduced using lipofectamine. Since up to date lipofection was the best gene transfer method to introduce plasmid DNA into DC, this experiment demonstrates that PEI is the most efficient non viral gene delivery system to transfer genes into DC. However, both PEI and lipofectamine exhibited significant toxicity to dendritic cells, as measured by tripan blue staining.

6. Specifically Targeting DC via Mannose Receptor

Immature DC were generated as described above in Example 1 and transfected with DNA encoding a green fluorescent protein (GFP). We used this DNA as a marker for gene expression, because cells expressing the green fluorescent protein light up green after the fluorescent stimulation. Therefore, transfected cells can be visualized by fluorescent microscopy and flow cytometry (FACS).

PEI modified with different sugars was chosen to target the mannose receptor on the surface of dendritic cells because the mannose receptor recognizes all the patterns of sugars on the surface of bacteria, parasites, yeast and fungi. DNA was complexed with PEI and with different sugar-bearing polyethylenimines (available on a custom order basis from Dr. Jean-Paul Behr, Laboratoire de Chimie Genetique, Faculte de Pharmacie, CNRS-UMR 7514 74 route du Rhin 67401 Illkirch, France). 2 microgram DNA was incubated with different derivates of PEI in 150 mM NaCl (10:1 N:P ratio) at room temperature for about 5 minutes. Than DC were transduced with the complexes for 6 hours washed, and green fluorescent cells were analyzed after 48 hours. We found that the most effective PEI-sugar modification is the PEI-mannose (Table 1).

TABLE 1

Different Complexes for in vitro Transduction of Dendritic cells

| Experiment | % of cells expressing green fluorescent protein |
|---|---|
| 1. Control | 4 |
| 3. PEI-mannose-DNA | 43 |
| 4. PEI-galactose-DNA | 23 |
| 5. PEI-glucose-DNA | 19 |

7. In Vitro PEI-Mannose-mediated Gene Transfer into Cultured Dendritic Cells

The mannose-bearing polyethylenimine (PEI-man) is an isothiocyanantophenyl phenyl mannose derivative, coupled to PEI 25 kDa, yielding a ligand (or, mannose residue of low affinity for the mannose receptor, 1 mM). It has been previously demonstrated that entry via the asialoglycoprotein receptor (used by PEI) requires the complex to be charged. That is, more PEI than DNA must be used. When the complex is neutralized, that is, the PEI is neutralized by the DNA, the complex cannot enter via the asialoglycoprotein receptor. [Zanta M A; Boussif O; Adib A; Behr J P. Bioconjug Chem November–December 1997; 8(6):839–44]: These investigators developed a hepatocyte-directed complex; it includes several key features thought to favoring vivo gene delivery to the liver: 1) electrostatically neutral particles which avoid nonspecific binding to other cells, and 2) to avoid asialoglycoprotein receptor-mediated endocytosis. This system was based on a 5% galactose-bearing polyethylenimine (PEI-gal) polymer which is condensed with plasmid DNA to neutrality.

We found that, with PEI-man-DNA complexes, less DNA is required to neutralize PEI-man compared to PEI. Gel electrophoresis experiments using different N:P ratio of PEI-DNA complexes demonstrated that 5:1 (N:P) of PEI-man:DNA complex has neutral charge, in contrast to 3:1 (N:P) PEI-DNA complex. {The neutralization of PEI with the DNA depends on the N(nitrogen):P(phosphate) ratio; one microgram DNA=3×109 molar P and 1 mM PEI=109 molar N/microliter. This means for example that 10:1 ratio is the mixture of 3 microliter 10 mM PEI and 1 microgram DNA.}

Human DC were isolated as described above. Purity of DC, characterized by FACS, was over 99%. By measuring cell viability with tripan-blue staining, we found that PEI-man was much less toxic than PEI. We also found that both PEI and PEI-man are able to introduce DNA into DC, however PEI-mannose is more efficient. At 5:1 (N:P) ratio PEI-man-DNA complex is neutral, therefore the complex is only able to enter into DC via the mannose receptor. Under these conditions, 30% of the DC were expressing the green fluorescent protein. In contrast, 5:1 (N:P) ratio PEI-DNA complex is charged and the complex enters via asialoglycoprotein receptor. Under this condition, 14% of the DC expressed the green fluorescent protein (FIG. 4).

8. In Vivo Gene Delivery to Skin Langerhans Cells

In the skin, the only cells which can endocytose mannosylated ligands are the Langerhans cells. Therefore, the main question was whether the PEI-(man) complex can penetrate into the skin and transfect Langerhans cells in vivo. PEI-(man) was complexed with plasmid DNA encoding a green fluorescent protein (GFP). Experiments with different gene delivery complexes were performed as described in FIG. 3. The complex contained 50 microgram DNA and 8.25 microliter 100 mM PEI-man in a 5–10% glucose solution (optimum=8%). BALB/c mice were anaesthetized, and the backs of the mice were shaved. 0.1 ml of the complexes were applied on the skin for one hour or subcutaneously as indicated in the Table 2. Mice were sacrificed 6 hours after immunization and skin samples were placed in DMEM media supplemented with 10% fetal calf serum and antibiotics. Under these conditions cells, including Langerhans cells migrate out from the skin. One day later the migrating cells were collected and analyzed by flow cytometry (FACS), because this analysis can recognize cells expressing the green fluorescent protein. In our analysis only the large and dense cell population was analyzed, because both dendritic cells and Langerhans cells are known to be large, dense cells.

TABLE 2

In vivo transduction of skin Langerhans cells

| Experiment | % of cells expressing green fluorescent protein |
|---|---|
| 1. Control | 0.84 |
| 2. Subcutaneous PEI-DNA | 0.20 |
| 3. Subcutaneous DNA | 1.74 |
| 4. Transcutaneous PEI-DNA | 6.52 |
| 5. Transcutaneous DNA | 29.10 |
| 6. Transcutaneous PEI-man-DNA | 22.99 |

These experiments demonstrate that 1) transcutaneous gene delivery results in more efficient gene transfer into Langerhans cells than subcutaneous delivery (compare experiment 2 & 4 or 3 & 5). This is important, because one of the best present vaccination technologies uses subcutaneous injection. 2) Entry via mannose receptors is more efficient to transfect in vivo Langerhans cells than entry via asialoglycoprotein receptor (compare experiment 4 & 6). These in vivo experiments confirm our in vitro experiment (see FIG. 4). Therefore, the sugar modified gene delivery system is preferred to transduce antigen presenting cells.

9. Transduced Langerhans Cells Migrate to the Lymph Nodes

Figure 7:
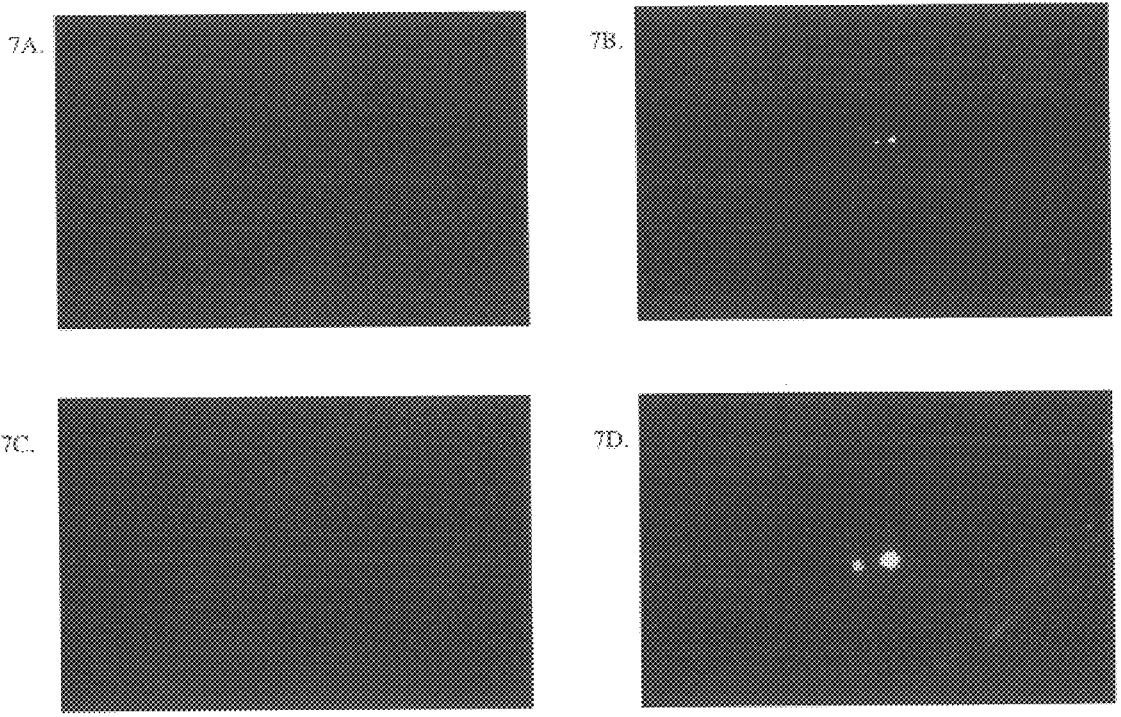
FIGS. 7A–7D is a color photograph showing that transcutaneous genetic immunization results in gene expression in the lymphoid organs.

BALB/c mice were prepared as in Example 8, and 0.1 ml samples of the PEI-man-DNA complex were applied on the skin for one hour. 2 days later the animals were sacrificed and lymph nodes (LN) were removed. Auxiliary LN were investigated because they are the draining LN of the back, and migrating Langerhans cells might be found there. The LN were frozen, sliced and examined under fluorescent microscope. The LN of experimental mice were compared with the LN of a control mouse. FIG. 7 demonstrates green fluorescent cells in the LN of the experimental animal. We were able to detect about 15 green fluorescent cells in the samples from the experimental LN and none in the control LN. These results demonstrate that the complex entered into cells located in the skin, and the cells were able to migrate into the LN and express the green fluorescent protein. The morphology of these green cells resembles DC morphology: these are big cells and the localization of the green fluorescence shows a "bumpy" pattern, which is characteristic to DC. (Other cells, e.g. 293 cells show a diffused green pattern in the cytoplasm.) In addition, the only cell type is able to pick up antigens and migrate to the LN is the Langerhans cell. These cells are the only cells in the skin to bear the mannose receptor in order to take up the complex and after activation is known that they are migrating in the draining LN.

These experiments show that PEI-(Man)-DNA complexes are able to penetrate in the skin, and deliver the DNA into Langerhans cells. The Langerhans cells were activated and migrated into the draining LN and expressed genes encoded by the DNA construct in the LN. It is known that cultured DC reinjected to the body migrate in the LN and generate efficient immune response. This invention demonstrates that in vitro isolation of DC is not required to transfer genes into Langerhans cells, or for gene expression in the lymphoid organs. We have also demonstrated that expression of a replication defective virus in DC results in efficient induction of a CTL response in vitro and in vivo (see above). Therefore, we have shown that transcutaneous gene delivery with complexes (like PEI-man-DNA) can be utilized to generate immune responses against proteins encoded in the DNA.

10. Sugar-DNA Complexes to Transduce Skin Langerhans Cells

Experimental results depicted in Table 2 provided evidence that a sugar-DNA complex, in the absence of PEI-man, can transduce Langerhans cells in vivo. Sugar complexed DNA in the absence of PEI is more efficient for use in both subcutaneous and transcutaneous methods than DNA complexed with PEI (see Table 2, experiments 3 & 5). This is a very surprising result. It shows that sugars (e.g. 8% glucose in these experiments) can also complex DNA and deliver the DNA to the Langerhans cells via the mannose receptor. Importantly, the most efficient gene delivery in vivo to the Langerhans cells was the sugar complexed DNA used in the transcutaneous way.

We expect that immunization with the sugar-DNA complex would also result in migration of the Langerhans cells to the draining lymph node. The reason is that the same mechanism is utilized for entry to Langerhans cells: mannose-receptor mediated uptake. The advantage of using sugars as adjuvants in the presently used vaccination technologies is that higher percentages of Langerhans cells will be involved in generation of immune response. This is expected to significantly increase the efficacy of present vaccination strategies. For example, mixing vaccines with sugar for subcutaneous, intradermal and intramuscular injections of DNA and protein antigens.

11. Implications of Transcutaneous Immunization

This technology would revolutionize the immunization methods because no needles are required. The described transcutaneous immunization is a very simple technology which could be used for inexpensive vaccination in both the developed and developing world.

The simplicity of the methodology and the fact that the antigen presenting cells are transduced efficiently enables us to use any DNA sequence able to generate an immunogenic protein. Thereby, the broadest spectrum of diseases can become target of immunization, e.g. infectious diseases and cancer.

The only way to eradicate infectious diseases, like HIV infection, hepatitis, malaria, is a simple inexpensive vaccination.

Vaccines without needle sticks will be expecially welcome to the parents of small children.

Use of the present invention potentially allows the development of safer vaccines. The few negative reactions to classical vaccines are sometimes due to an allergic reaction to byproducts of the vaccine manufacturing process. Where such additional materials (egg albumin, for example) can be eliminated, the rate of negative reactions can be concomitantly reduced.

It can be used for immunization for the treatment of diseases with or without combination chemotherapy.

What is claimed is:

1. A gene delivery complex comprising DNA and mannosylated polyethylenimine, wherein said DNA comprises a nucleic acid sequence encoding at least one immunogenic protein operatively linked to a promoter.

2. The gene delivery complex of claim 1, wherein the immunogenic protein is derived from a reverse transcriptase-dependent virus.

3. The gene delivery complex of claim 2, wherein the reverse transcriptase-dependent virus is a human immunodeficiency virus.

4. The gene delivery complex of claim 3, wherein the human immunodeficiency virus is replication-defective.

5. The gene delivery complex of claim 3, wherein the human immunodeficiency virus is integration-defective.

6. A composition for delivering DNA into antigen presenting cells comprising a glucose solution, DNA, and mannosylated polyethylenimine, wherein said DNA comprises a nucleic acid sequence encoding at least one protein operatively linked to a promoter.

7. The composition of claim 6, wherein the mannosylated polyethylenimine is an isothiocyanantophenyl phenyl mannose derivative coupled to PEI 25 kDA.

8. The composition of claim 6, wherein the protein is an immunogenic protein.

9. The composition of claim 6, wherein the immunogenic protein is derived from a reverse transcriptase-dependent virus.

10. The composition of claim 6, wherein the protein is derived from a virus.

11. The composition of claim 10, wherein the virus is a replication- or integration-defective, reverse transcriptase-dependent virus.

12. The composition of claim 6, wherein the protein is an immunogenic protein from a human immunodeficiency virus.

13. The composition of claim 12, wherein the human immunodeficiency virus is an integrase-defective human immunodeficiency virus.

14. The composition of claim 1 or 6, wherein the DNA is a plasmid.

* * * * *